United States Patent [19]

Kohler

[11] 4,139,280

[45] Feb. 13, 1979

[54] HEAD REST FOR OPHTHALMOLOGICAL EXAMINATION

[75] Inventor: Kurt Köhler, Königsbronn, Fed. Rep. of Germany

[73] Assignee: Carl Zeiss-Stiftung, Oberkochen, Fed. Rep. of Germany

[21] Appl. No.: 703,283

[22] Filed: Jul. 7, 1976

[30] Foreign Application Priority Data

Sep. 3, 1975 [DE] Fed. Rep. of Germany ... 7527790[U]

[51] Int. Cl.² .............................................. A61B 3/00
[52] U.S. Cl. .................................... 351/38; 248/188.4
[58] Field of Search .................. 351/38, 23, 24, 17, 351/14; 250/451, 456; 297/391, 410; 248/274, 188.4

[56] References Cited

U.S. PATENT DOCUMENTS

| 2,999,422 | 9/1961 | Papritz | 351/38 |
| 3,594,072 | 7/1971 | Feather | 351/39 |

OTHER PUBLICATIONS

Romuald Schön, A New Compound-Stage with Head Rest, Jena Review, No. 2, 1969, pp. 142–144.
Topcon Instrument Corp. of America, Journal of the Amer. Optometric Assoc., 2/75.

*Primary Examiner*—Paul A. Sacher
*Attorney, Agent, or Firm*—Hopgood, Calimafde, Kalil, Blaustein & Lieberman

[57] ABSTRACT

A head rest for instruments used for opthamological examination comprises two vertical columns mounted on the instrument base. Each of said columns carries a vertical post to which is attached a forehead rest spanning the space between the posts. Said posts are retracted with respect to said columns. Said columns also carry a transverse bar spanning the space between the columns and supporting a chin rest which is adjustable with respect to the base. The arrangement provides maximum freedom of movement around the patient's eyes for the physician or surgeon.

2 Claims, 3 Drawing Figures

HEAD REST FOR OPHTHALMOLOGICAL EXAMINATION

This invention relates to a head rest for instruments used for ophthalmological examinations, which comprises two columns mounted on a instrument base, a chin rest, and a forehead rest mounted on said columns. The chin rest is adjustable to vary the height of the chin rest with respect to the base.

In ophthalmological examinations, especially in tonometry and in contact lens fitting, maximum of freedom of movement around the patient's eyes is desirable for the physician or surgeon.

Various types of head rests are known which are used to facilitate eye examinations with ophthalmological instruments. Such known head rests are usually equipped with facilities for manual or motorized height adjustment of the chin rest. Moreover, forehead rests are available to ensure that the patient holds his head steady. However, the more popular head rests are so designed that the upper ends of the vertical columns or supports for holding chin and forehead rests are about as high as the patient's forehead, and these columns are so attached to the base that they are close to the patient's eyes. The surgeon's freedom of movement around the patient's eyes is thus considerably restricted.

An object of the invention is, therefore, to provide a head rest which permits greater freedom of movement for the surgeon than is possible in using the available head rests.

According to the invention, this object is achieved by providing each of the two columns attached to the instrument base with a vertical post for supporting the forehead rest which is fixed to the columns below the patient's chin level in such a way that, seen from the side of the surgeon, the plane defined by the vertical posts for the forehead rest is retracted relative to the plane defined by the front of the columns to the extent that the patient's eyes are freely accessible. That is, the posts are offset rearwardly from the columns.

In a preferred embodiment of the invention, a transverse bar is attached to the columns for holding the chin rest and is shaped in such a way that the chin rest is located in a plane which, seen from the side of the surgeon, is also retracted relative to the plane defined by the front faces of the columns.

For vertical adjustment of the transverse bar holding the chin rest, a preferred embodiment of the invention incorporates in one column an elevating screw with nut and in the other a spindle carried in a sliding bearing.

The principal advantage of the invention is the great freedom of movement for the surgeon achieved around the patient's eyes.

In a head rest according to the present invention, the vertical posts which in conventional head rest versions are arranged near the temples, are retracted to such an extent that they are located close to the patient's ears and, thus, offer no obstruction for the surgeon. Moreover, the transverse bar is so designed that it makes a suitable hand rest for the surgeon. The knurled knob for vertical adjustment of the chin rest is within easy reach.

A preferred embodiment of the invention is shown in the accompanying drawings in which.

Figure 1:
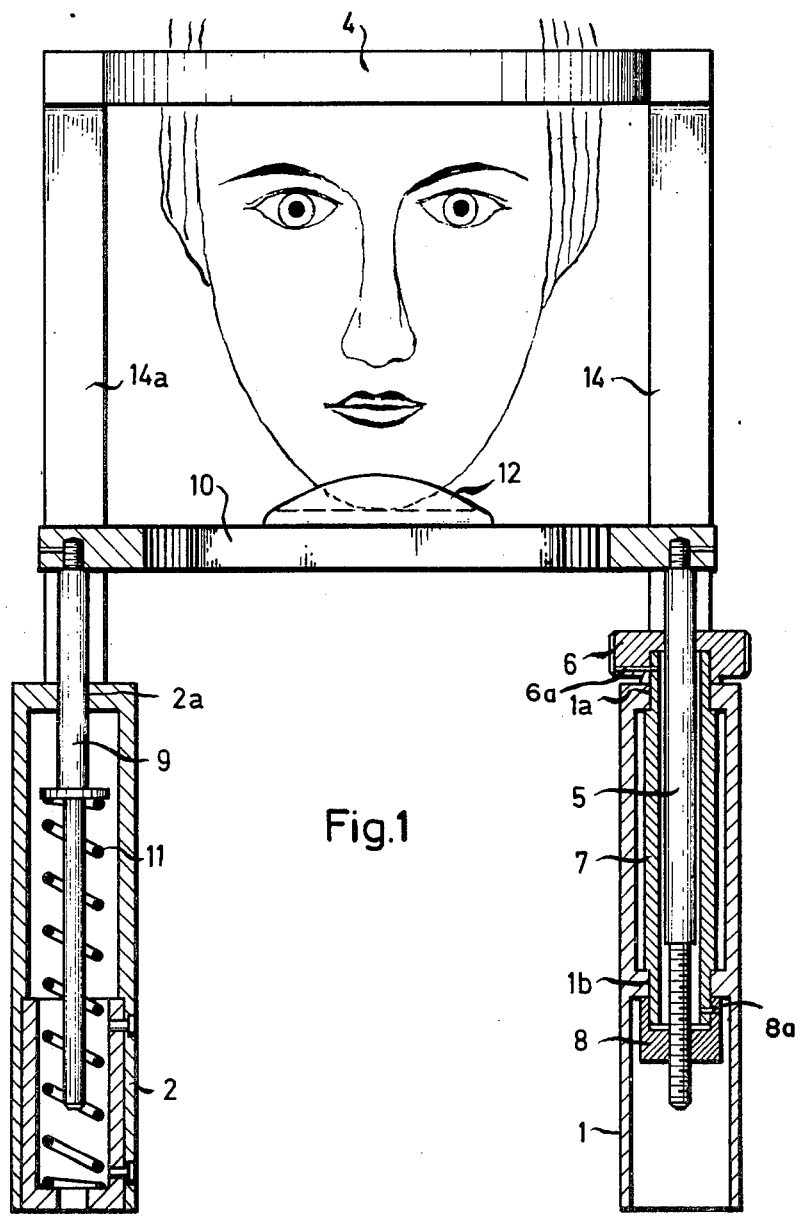
FIG. 1 is a front elevation of the head rest of the present invention.
Figure 2:
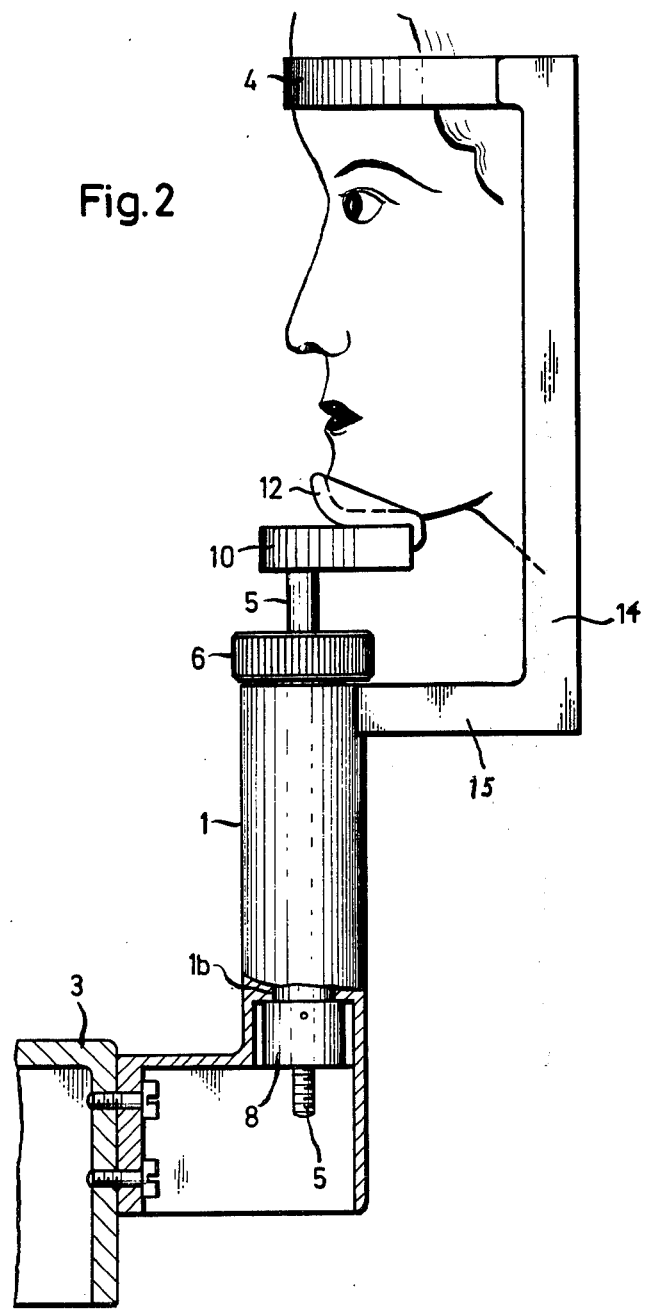
FIG. 2 is a side elevation, partly in section, of the right side of the head rest.
Figure 3:
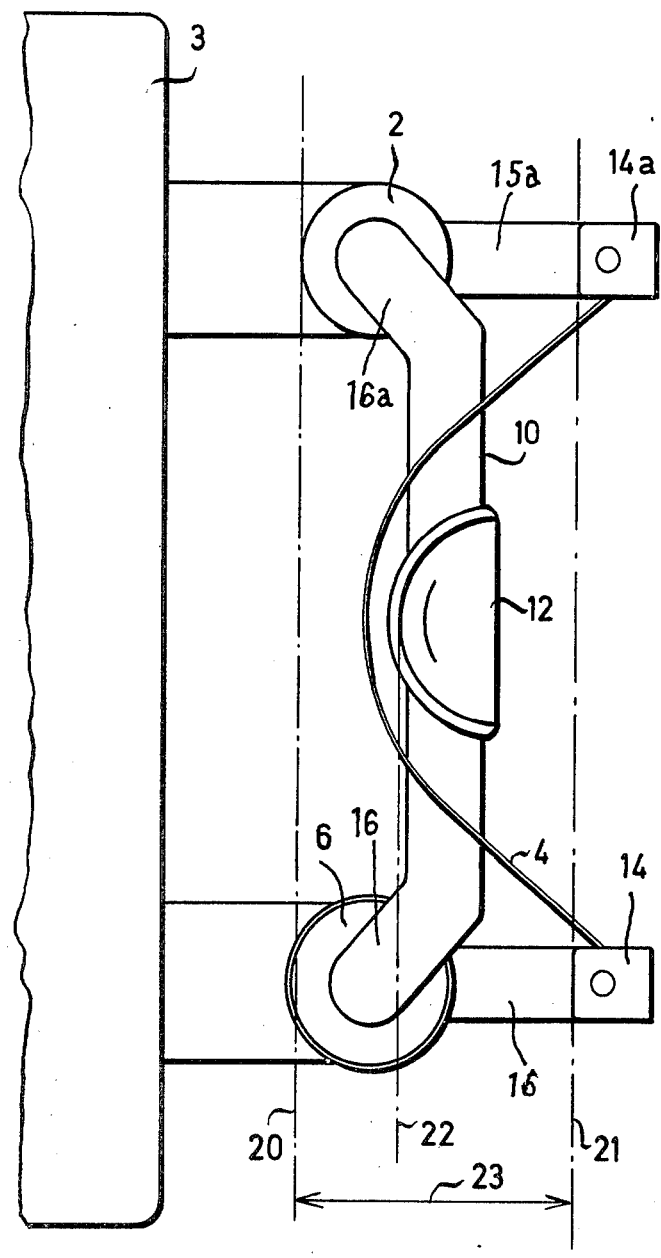
FIG. 3 is a top plan view of the head rest.

Referring to the drawings, 3 indicates the instrument base which is shown only in FIGS. 2 and 3. Mounted on the instrument base 3 are columns 1 and 2 which are connected by a transverse bar 10 spanning the space between said columns and holding chin rest 12. Posts 14 and 14a which carry the forehead rest 4 are attached to the columns 1 and 2, respectively, by horizontal arms 15 and 15a which extend at right angles thereto. A suitable flexible band 4 of a plastic material such as Teflon is attached to the posts 14, 14a and serve as a forehead rest. For vertical adjustment of the chin rest, column 1 houses a threaded nut 8 engaged with elevating screw 5 and actuated by a knurled knob 6; the reduced ends of a tube 7 have spaced rotary support in column 1 at 1a-1b and are pinned at 6a-8a to connect knob 6 to nut 8. Column 2, which is connected with column 1 by transverse bar 10, is equipped with a vertical spindle 9 which slide in a bearing 2a and is surrounded by a cylindrical helical spring 11. By turning knurled knob 6, elevating screw 5 is moved vertically together with transverse bar 10 and spindle 9.

The central portion of the bar 10 is connected to the columns 1, 2 by side arms 16, 16a which extend laterally and forwardly from the central portion so that the chin rest 12 is retracted with respect to the columns 1, 2, being located behind the central axes of the columns.

The vertical view in FIG. 3 shows planes 20, 21 and 22 in broken lines. Plane 20 is tangent to the front surfaces of columns 1 and 2 facing the surgeon. Plane 21 touches the front surfaces of posts 14 and 14a facing the surgeon. The free examination space gained by the special way of attaching posts 14 and 14a to columns 1 and 2 is indicated by distance 23. Plane 22 is tangent to the surface of the chin rest engaged by the chin of the patient.

What is claimed is:

1. A head rest for an instrument used for ophthalmological examinations comprising two vertical columns mounted in spaced relation on the base of said instrument, a vertical post mounted on each of said vertical columns, a forehead rest mounted on said vertical posts and spanning the space therebetween, said posts being offset rearwardly from said columns, a transverse bar mounted on said columns and spanning the space therebetween, a chin rest mounted on said transverse bar, said chin rest being located in front of and offset from said posts, and means for elevating said transverse bar with respect to said columns, said elevating means comprising an elevating screw and nut mounted in one of said columns and a spindle which slides in a bearing in the other of said columns.

2. A head rest according to claim 1, and including a helical spring compressionally reacting between said base and spindle.

* * * * *